(12) United States Patent
Yamamoto

(10) Patent No.: US 11,713,294 B2
(45) Date of Patent: Aug. 1, 2023

(54) METHOD FOR PRODUCING ORGANIC TELLURIUM COMPOUND AND METHOD FOR PRODUCING VINYL POLYMER

(71) Applicant: OTSUKA CHEMICAL CO., LTD, Osaka (JP)

(72) Inventor: Minoru Yamamoto, Tokushima (JP)

(73) Assignee: OTSUKA CHEMICAL CO., LTD, Osaka (JP)

( * ) Notice: Subject to any disclaimer, the term of this patent is extended or adjusted under 35 U.S.C. 154(b) by 252 days.

(21) Appl. No.: 17/294,866

(22) PCT Filed: Nov. 19, 2019

(86) PCT No.: PCT/JP2019/045167
§ 371 (c)(1),
(2) Date: May 18, 2021

(87) PCT Pub. No.: WO2020/116144
PCT Pub. Date: Jun. 11, 2020

(65) Prior Publication Data
US 2022/0009885 A1    Jan. 13, 2022

(30) Foreign Application Priority Data

Dec. 5, 2018   (JP) ................. 2018-228214

(51) Int. Cl.
C07C 395/00     (2006.01)
C08F 4/42       (2006.01)
C08F 20/14      (2006.01)

(52) U.S. Cl.
CPC .............. C07C 395/00 (2013.01); C08F 4/42 (2013.01); C08F 20/14 (2013.01)

(58) Field of Classification Search
CPC ........... C07C 395/00; C08F 20/14; C08F 4/42
See application file for complete search history.

(56) References Cited

U.S. PATENT DOCUMENTS

| | | | |
|---|---|---|---|
| 2005/0245714 A1 | 11/2005 | Yamago et al. | |
| 2008/0004366 A1 | 1/2008 | Yamago et al. | |
| 2015/0152212 A1 | 6/2015 | Umemoto | |
| 2020/0048192 A1* | 2/2020 | Yamago ................ | C08F 120/20 |

FOREIGN PATENT DOCUMENTS

| | | | | |
|---|---|---|---|---|
| CN | 1649838 A | 8/2005 | | |
| EP | 2 009 030 A1 | 12/2008 | | |
| EP | 2009030 A1 * | 12/2008 | .......... | C08F 293/005 |
| JP | 2004-323437 A | 11/2004 | | |
| JP | 2013-119568 A | 6/2013 | | |
| WO | 2004/014848 A1 | 2/2004 | | |
| WO | WO-2004014848 A1 * | 2/2004 | .......... | C07C 395/00 |
| WO | 2007/119884 A1 | 10/2007 | | |
| WO | 2018/199000 A1 | 11/2018 | | |
| WO | WO-2018199000 A1 * | 11/2018 | .......... | C07C 395/00 |

OTHER PUBLICATIONS

Yamago et al., JACS, (Feb. 2020), vol. 124, No. 12, pp. 2874-2875. (Year: 2020).*
Notification of Transmittal of Translation of the International Preliminary Report on Patentability (Form PCT/IB/338) issued in counterpart International Application No. PCT/JP2019/045167 dated Jun. 10, 2021 with Form PCT/IPEA/409. (5 pages).
International Search Report dated Feb. 10, 2020, issued in counterpart International Application No. PCT/JP2019/045167. (3 pages).
Yamago et al., "Organotellurium Compounds as Novel Initiators for Controlled/Living Radical Polymerizations. Synthesis of Functionalized Polystyrenes and End-Group Modifications", Journal of the American Chemical Society, Feb. 27, 2002, vol. 124, No. 12, pp. 2874-2875. Cited in ISR. (3 pages).
Silks et al., "Synthesis and 125 Te NMR Spectroscopy of a-Tellurocarbonyl Compounds and Derivatives", Synthetic Communications, (1991), vol. 21, No. 8, 9, pp. 1105-1119. Cited in ISR. (15 pages).
Ohyanagi et al., "Compact and stable SNAP ligand-conjugated quantum dots as a fluorescent probe for single-molecule imaging of dynein motor protein", Chemical Communications, (2015), vol. 51, No. 80, pp. 14836-14839. Cited in ISR. (14 pages).
Office Action dated Dec. 8, 2022, issued in counterpart IN application No. 202117026091, with English translation. (6 pages).
Extended (Supplementary) European Search Report dated Aug. 30, 2022, issued in counterpart EP application No. 19894322.7. (7 pages).
Office Action dated Sep. 27, 2022, issued in counterpart CN application No. 201980077420.0. (7 pages).

* cited by examiner

Primary Examiner — Robert D Harlan
(74) Attorney, Agent, or Firm — WHDA, LLP

(57) ABSTRACT

Provided is a method for producing an organic tellurium compound that enables the production of an organic tellurium compound in high yield using metallic tellurium as a source material and produces less amount of side products. A method for producing an organic tellurium compound includes the steps of: (A) reacting metallic tellurium with a compound represented by a general formula (1) below; and (B) reacting a compound obtained by the step (A) with an organic halogen compound, the metallic tellurium having a copper content of less than 100 ppm, $$M(R^1)m \qquad \text{Formula (1)}$$

where $R^1$ represents an alkyl group having 1 to 8 carbon atoms, an aryl group or an aromatic heterocyclic group, M represents an alkali metal or an alkaline earth metal, m represents 1 when M is an alkali metal, and m represents 2 when M is an alkaline earth metal.

10 Claims, No Drawings

METHOD FOR PRODUCING ORGANIC TELLURIUM COMPOUND AND METHOD FOR PRODUCING VINYL POLYMER

TECHNICAL FIELD

The present invention relates to methods for producing organic tellurium compounds and methods for producing vinyl polymers.

BACKGROUND ART

Living radical polymerization processes are polymerization processes that enable precise control of molecular structures and production of polymers having a homogeneous composition while keeping the convenience and versatility of conventional radical polymerization processes, and demonstrate superior performance on production of novel polymeric materials. Therefore, living radical polymerization techniques have recently progressed greatly and living radical polymerization processes using various approaches have been reported. The living radical polymerization process is classified, for example, in terms of differences in the approach for stabilizing growing ends of polymerization, into a process using a transition metal catalyst (ATRP process), a process using a sulfur-based, reversible chain transfer agent (RAFT process), and a process using an organic tellurium compound (TERP process). Among these processes, the TERP process is a polymerization process to which particular attention has been paid from the viewpoints of the variety of usable monomers, molecular weight control in a high molecular weight region, and homogeneous composition, and polymers produced using the TERP process are widely used for a pressure-sensitive adhesive, a pigment dispersant, and so on (see Patent Literatures 1 and 2).

Meanwhile, there are known, as methods for producing organic tellurium compounds for use in the TERP process, for example, a method of reacting an organic ditelluride compound with an azo polymerization initiator (see Patent Literature 3) and a method of reacting metallic tellurium, an organic metal compound, and an organic halogen compound (see Patent Literature 4).

CITATION LIST

Patent Literature

Patent Literature 1: WO 2007/119884
Patent Literature 2: JP-A-2013-119568
Patent Literature 3: JP-A-2004-323437
Patent Literature 4: WO 2004/014848

SUMMARY OF INVENTION

Technical Problem

However, the method in Patent Literature 3 requires preliminary synthesis of an organic ditelluride compound and, therefore, it is difficult to say that the method is a convenient production method. In addition, the yield of an organic tellurium compound is low. The method in Patent Literature 4 is a convenient production method, but its yield of an organic tellurium compound is insufficient.

Furthermore, the inventors found that side products (impurities) contained in the organic tellurium compound obtained by the method in Patent Literature 4 may cause coloration of a vinyl polymer obtained by a living radical polymerization process using the organic tellurium compound, which causes a problem of an adverse effect on the quality of a final product, such as a pressure-sensitive adhesive or a pigment dispersant. However, the removal of the side products was not easy.

The present invention has been made in view of the foregoing circumstances and has an object of providing: a method for producing an organic tellurium compound that enables the production of an organic tellurium compound in high yield using metallic tellurium as a source material and produces less amount of side products; and a method for producing a vinyl polymer.

Solution to Problem

The inventors conducted intensive studies to solve the above problem and completed the present invention. Specifically, the gist of the present invention is as follows.

Aspect 1: A method for producing an organic tellurium compound, the method including the steps of: (A) reacting metallic tellurium with a compound represented by a general formula (1) below; and (B) reacting a compound obtained by the step (A) with an organic halogen compound, the metallic tellurium having a copper content of less than 100 ppm.

$$M(R^1)m \qquad \text{Formula (1)}$$

In the formula (1), $R^1$ represents an alkyl group having 1 to 8 carbon atoms, an aryl group or an aromatic heterocyclic group, M represents an alkali metal or an alkaline earth metal, m represents 1 when M is an alkali metal, and m represents 2 when M is an alkaline earth metal.

Aspect 2: The method for producing an organic tellurium compound according to aspect 1, wherein the copper content of the metallic tellurium is equal to or more than 0.1 ppm and less than 100 ppm.

Aspect 3: The method for producing an organic tellurium compound according to aspect 1 or 2, wherein an oxygen content of the metallic tellurium is less than 3%.

Aspect 4: The method for producing an organic tellurium compound according to aspect 3, wherein the oxygen content of the metallic tellurium is equal to or more than 0.1% and less than 3%.

Aspect 5: The method for producing an organic tellurium compound according to any one of aspects 1 to 4, wherein the organic halogen compound is at least one selected from the group consisting of a compound represented by a general formula (2-1) below and a compound represented by a general formula (2-2) below.

[Chem. 1]

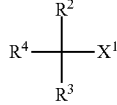

Formula (2-1)

In the formula (2-1), $R^2$ and $R^3$ each independently represent a hydrogen atom or an alkyl group having 1 to 8 carbon atoms, $R^4$ represents an alkyl group having 1 to 8 carbon atoms, an aryl group, a substituted aryl group, an aromatic heterocyclic group, an alkoxy group, an acyl group, an amide group, an oxycarbonyl group, a cyano group, an allyl group or a propargyl group, and $X^1$ represents a halogen atom.

[Chem. 2]

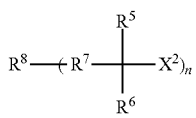

Formula (2-2)

In the formula (2-2), $R^5$ and $R^6$ each independently represent a hydrogen atom or an alkyl group having 1 to 8 carbon atoms, $X^2$ represents a halogen atom, $R^7$ represents an alkylene group having 1 to 8 carbon atoms, an arylene group, an amide group or an ester group, n is an integer of 2 to 4, and $R^8$ represents a divalent single bond or a divalent organic group when n is 2, represents a trivalent organic group when n is 3, and represents a tetravalent organic group when n is 4.

Aspect 6: The method for producing an organic tellurium compound according to any one of aspects 1 to 5, wherein a usage rate of the compound represented by the general formula (1) is 0.5 mol to 1.5 mol per mole of the metallic tellurium.

Aspect 7: The method for producing an organic tellurium compound according to any one of aspects 1 to 6, wherein a usage rate of the organic halogen compound is 0.5 mol to 6 mol per mole of the metallic tellurium.

Aspect 8: The method for producing an organic tellurium compound according to anyone of aspects 1 to 7, wherein a specific surface area of the metallic tellurium is 0.5 m²/g to 2.0 m²/g.

Aspect 9: The method for producing an organic tellurium compound according to anyone of aspects 1 to 8, wherein the step (A) is performed by suspending the metallic tellurium in a solvent.

Aspect 10: The method for producing an organic tellurium compound according to aspect 9, wherein the solvent is an aprotic polar solvent.

Aspect 11: The method for producing an organic tellurium compound according to aspect 9 or 10, wherein the solvent is at least one selected from the group consisting of tetrahydrofuran, acetone, acetonitrile, N,N-dimethylformamide, dimethylsulfoxide, N-methyl-2-pyrrolidone, N,N-dimethylacetamide, and 1,3-dimethyl-2-imidazolidinone.

Aspect 12: The method for producing an organic tellurium compound according to any one of aspects 1 to 11, wherein a reaction temperature in the step (A) is −20° C. to 80° C. and a reaction temperature in the step (B) is −20° C. to 80° C.

Aspect 13: The method for producing an organic tellurium compound according to any one of aspects 1 to 12, the method being a method for producing an organic tellurium compound represented by a general formula (5-1) below or an organic tellurium compound represented by a general formula (5-2) below.

[Chem. 3]

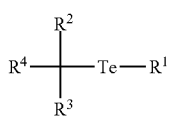

Formula (5-1)

In the formula (5-1), $R^1$ represents an alkyl group having 1 to 8 carbon atoms, an aryl group or an aromatic heterocyclic group, $R^2$ and $R^3$ each independently represent a hydrogen atom or an alkyl group having 1 to 8 carbon atoms, and $R^4$ represents an alkyl group having 1 to 8 carbon atoms, an aryl group, a substituted aryl group, an aromatic heterocyclic group, an alkoxy group, an acyl group, an amide group, an oxycarbonyl group, a cyano group, an allyl group or a propargyl group.

[Chem. 4]

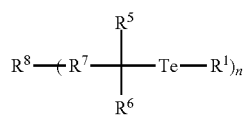

Formula (5-2)

In the formula (5-2), $R^1$ represents an alkyl group having 1 to 8 carbon atoms, an aryl group or an aromatic heterocyclic group, $R^5$ and $R^6$ each independently represent a hydrogen atom or an alkyl group having 1 to 8 carbon atoms, $R^7$ represents an alkylene group having 1 to 8 carbon atoms, an arylene group, an amide group or an ester group, $R^8$ represents a divalent single bond or a divalent organic group when n is 2, represents a trivalent organic group when n is 3, and represents a tetravalent organic group when n is 4.

Aspect 14: A living radical polymerization initiator being an organic tellurium compound obtained by the method according to any one of aspects 1 to 13.

Aspect 15: A method for producing a vinyl polymer, the method including the step of polymerizing a vinyl monomer by living radical polymerization using the organic tellurium compound obtained by the method according to any one of aspects 1 to 13 to synthesize a vinyl polymer.

Aspect 16: A vinyl polymer produced by the method for producing a vinyl polymer according to aspect 15.

Advantageous Effects of Invention

The present invention enables provision of a method for producing an organic tellurium compound that enables the production of an organic tellurium compound in high yield using metallic tellurium as a source material and produces less amount of side products. Furthermore, by polymerizing a vinyl monomer using the organic tellurium compound obtained by the production method according to the present invention, coloration of a vinyl polymer can be reduced.

Description of Embodiments

Hereinafter, a description will be given of an example of a preferred embodiment for working of the present invention. However, the following embodiment is simply illustrative. The present invention is not at all limited by the following embodiment.

<Method for Producing Organic Tellurium Compound>

A method for producing an organic tellurium compound according to the present invention is a production method including the steps of: (A) reacting metallic tellurium with a compound represented by a general formula (1); and (B) reacting a compound obtained by the step (A) with an organic halogen compound.

(Step (A))

The step (A) is the step of reacting metallic tellurium with a compound represented by the general formula (1) below.

$$M(R^1)m \qquad \text{Formula (1)}$$

In the formula (1), $R^1$ represents an alkyl group having 1 to 8 carbon atoms, an aryl group or an aromatic heterocyclic group, M represents an alkali metal or an alkaline earth metal, m represents 1 when M is an alkali metal, and m represents 2 when M is an alkaline earth metal.

$R^1$ in the general formula (1) is an alkyl group having 1 to 8 carbon atoms, an aryl group or an aromatic heterocyclic group, and preferably an alkyl group having 1 to 8 carbon atoms. Specific examples of $R^1$ are as follows.

Examples of the alkyl group having 1 to 8 carbon atoms include: a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, and other linear or branched alkyl groups; and a cyclohexyl group and other cyclic alkyl groups. Preferred are linear or branched alkyl groups having 1 to 4 carbon atoms.

Examples of the aryl group include a phenyl group and a naphthyl group.

Examples of the aromatic heterocyclic group include a pyridyl group, a furyl group, and a thienyl group.

M in the general formula (1) is an alkali metal, such as lithium, sodium or potassium, or an alkaline earth metal, such as magnesium or calcium, preferably an alkali metal in light of reactivity, and more preferably lithium.

Specific examples of the compound represented by the general formula (1) include: methyl lithium, ethyl lithium, n-propyl lithium, isopropyl lithium, n-butyl lithium, and other alkyl lithiums; and phenyl lithium and other aryl lithiums.

The content (mass ratio) of copper in metallic tellurium for use in the present invention is less than 100 ppm, preferably not more than 90 ppm, more preferably not more than 70 ppm, still more preferably not more than 40 ppm, particularly preferably not more than 20 ppm, preferably not less than 0.1 ppm, more preferably not less than 1 ppm, still more preferably not less than 2 ppm, and particularly preferably not less than 10 ppm. The copper content can be measured with an ICP mass spectrometer.

The content (mass ratio) of oxygen in metallic tellurium for use in the present invention is preferably less than 3%, more preferably less than 2.5%, preferably not less than 0.1%, and more preferably not less than 0.5%. The oxygen content can be measured with an X-ray fluorescence spectrometer.

The metallic tellurium for use in the present invention can be used without limit so long as the copper content is in the above range. For example, it is possible to measure commercially available metallic telluriums in terms of copper content and oxygen content and selectively use one of them. Alternatively, it is possible to treat a commercially available metallic tellurium with acid or alkali to adjust its copper content and oxygen content and then use it.

The metallic tellurium for use in the present invention is preferably in powdered form in light of reactivity and its specific surface area is preferably 0.5 m²/g to 2.0 m²/g and more preferably 0.8 m²/g to 1.5 m²/g. The specific surface area can be measured by the BET method with a surface area analyzer.

Specifically, in the step (A), it is preferred that, under an inert gas atmosphere, metallic tellurium is suspended in a solvent to adjust a suspension, a compound represented by the general formula (1) is added into the suspension, and the suspension is stirred to yield a reaction.

The reaction time differs depending on the reaction temperature and the pressure, but is preferably 5 minutes to 24 hours and more preferably 10 minutes to 2 hours. The reaction temperature is preferably −20° C. to 80° C., more preferably −10° C. to 30° C., and still more preferably −5° C. to 15° C. The pressure is normally an ordinary pressure, but may be an increased pressure or a reduced pressure.

Examples of the inert gas include nitrogen, argon, and helium and preferred inert gases are argon and nitrogen. When the step (A) is performed under an inert gas atmosphere, the yield of an organic tellurium compound can be further increased and the production of side products can be further reduced.

Examples of the solvent include: aprotic polar solvents, such as tetrahydrofuran (THF), acetone, acetonitrile, N,N-dimethylformamide (DMF), dimethylsulfoxide (DMSO), N-methyl-2-pyrrolidone, N,N-dimethylacetamide, and 1,3-dimethyl-2-imidazolidinone; aromatic solvents, such as toluene and xylene; aliphatic hydrocarbons, such as hexane; and ethers, such as dialkyl ether, and the preferred solvents are aprotic polar solvents. The amount of solvent used is appropriately adjusted, but is preferably 5 ml to 10 ml and more preferably 7 ml to 10 ml per gram of metallic tellurium.

The usage rate of the compound represented by the general formula (1) is, per mole of metallic tellurium, preferably 0.5 mol to 1.5 mol and more preferably 0.8 mol to 1.2 mol.

(Step (B))

The step (B) is the step of reacting a compound obtained by the step (A) with an organic halogen compound.

The organic halogen compound that can be used is a monofunctional organic halogen compound or a multifunctional organic halogen compound. The term "monofunctional organic halogen compound" used herein refers to an "organic halogen compound containing one halogen atom per molecule", while the term "multifunctional organic halogen compound" used herein refers to an "organic halogen compound containing two or more halogen atoms per molecule".

The above types of organic halogen compounds can be used differently depending on the purpose. For example, a monofunctional organic halogen compound is used in producing a monofunctional living radical polymerization initiator, while a multifunctional organic halogen compound is used in producing a multifunctional living radical polymerization initiator.

For example, the organic halogen compound is at least one selected from the group consisting of a compound represented by a general formula (2-1) and a compound represented by a general formula (2-2), and is preferably a compound represented by the general formula (2-1).

The compound represented by the general formula (2-1) is described below.

[Chem. 5]

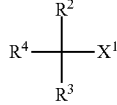

Formula (2-1)

In the formula (2-1), $R^2$ and $R^3$ each independently represent a hydrogen atom or an alkyl group having 1 to 8 carbon atoms, $R^4$ represents an alkyl group having 1 to 8 carbon atoms, an aryl group, a substituted aryl group, an aromatic heterocyclic group, an alkoxy group, an acyl group, an amide group, an oxycarbonyl group, a cyano group, an allyl group or a propargyl group, and $X^1$ represents a halogen atom.

The respective groups represented by $R^2$ and $R^3$ in the formula (2-1) are each independently a hydrogen atom or an alkyl group having 1 to 8 carbon atoms, and the groups are specifically as follows.

Examples of the alkyl group having 1 to 8 carbon atoms include: a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, and other linear or branched alkyl groups; and a cyclohexyl group and other cyclic alkyl groups. Linear or branched alkyl groups having 1 to 4 carbon atoms are preferred, and a methyl group or an ethyl group is more preferred.

The group represented by $R^4$ in the general formula (2-1) is an alkyl group having 1 to 8 carbon atoms, an aryl group, a substituted aryl group, an aromatic heterocyclic group, an alkoxy group, an acyl group, an amide group, an oxycarbonyl group, a cyano group, an allyl group or a propargyl group, and specifically as follows.

Examples of the alkyl group having 1 to 8 carbon atoms include: a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, and other linear or branched alkyl groups; and a cyclohexyl group and other cyclic alkyl groups. Linear or branched alkyl groups having 1 to 4 carbon atoms are preferred, and a methyl group or an ethyl group is more preferred.

Examples of the aryl group include a phenyl group and a naphthyl group. A phenyl group is preferred.

Examples of the substituted aryl group include a phenyl group with a substituent and a naphthyl group with a substituent . Examples of the substituent of the aryl group with a substituent include a halogen atom, a hydroxy group, an alkoxy group, an amino group, a nitro group, a cyano group, a carbonyl-containing group represented by —$COR^{41}$ (where $R^{41}$ is an alkyl group having 1 to 8 carbon atoms, an aryl group, an alkoxy group having 1 to 8 carbon atoms or an aryloxy group), a sulfonyl group, and a trifluoromethyl group. Furthermore, the number of substitutions in the aryl group with these types of substituent is preferably one or two.

Examples of the aromatic heterocyclic group include a pyridyl group, a furyl group, and a thienyl group.

The alkoxy group is preferably a group in which an alkyl group having 1 to 8 carbon atoms is bound to an oxygen atom, and examples include a methoxy group, an ethoxy group, a propoxy group, an isopropoxy group, an n-butoxy group, a sec-butoxy group, a tert-butoxy group, a pentyloxy group, a hexyloxy group, a heptyloxy group, and an octyloxy group.

Examples of the acyl group include an acetyl group, a propionyl group, and a benzoyl group.

An example of the amide group is —$CONR^{421}R^{422}$ (where $R^{421}$ and $R^{422}$ are each independently a hydrogen atom, an alkyl group having 1 to 8 carbon atoms or an aryl group).

The oxycarbonyl group is preferably a group represented by —$COOR^{43}$ (where $R^{43}$ is a hydrogen atom, an alkyl group having 1 to 8 carbon atoms or an aryl group) and examples include a carboxy group, a methoxycarbonyl group, an ethoxycarbonyl group, a propoxycarbonyl group, an n-butoxycarbonyl group, a sec-butoxycarbonyl group, a tert-butoxycarbonyl group, an n-pentoxycarbonyl group, and a phenoxycarbonyl group. Preferred oxycarbonyl groups include a methoxycarbonyl group and an ethoxycarbonyl group.

An example of the allyl group is —$CR^{441}R^{442}$—$CR^{443}$=$CR^{444}R^{445}$ (where $R^{441}$ and $R^{442}$ are each independently a hydrogen atom or an alkyl group having 1 to 8 carbon atoms, $R^{443}$, $R^{444}$, and $R^{445}$ are each independently a hydrogen atom, an alkyl group having 1 to 8 carbon atoms or an aryl group, and the substituents may be bound to each other in a cyclic structure).

An example of the propargyl group is —$CR^{451}R^{452}$—C≡$CR^{453}$ (where $R^{451}$ and $R^{452}$ are each independently a hydrogen atom or an alkyl group having 1 to 8 carbon atoms and $R^{453}$ is a hydrogen atom, an alkyl group having 1 to 8 carbon atoms, an aryl group or a silyl group).

The group represented by $X^1$ in the general formula (2-1) is a halogen atom, such as fluorine, chlorine, bromine or iodine, and is preferably a chlorine atom or a bromine atom.

Specific examples of the compound represented by the general formula (2-1) include ethyl-2-methyl-2-chloro-propionate, ethyl-2-methyl-2-bromo-propionate, ethyl-2-methyl-2-iodo-propionate, methyl-2-methyl-2-bromo-propionate, dimethylamino-2-methyl-2-bromo-propionate, 2-methyl-2-bromo-propionitrile, (1-bromo-ethyl)benzene, 1-bromo-1-methoxyhexane, 4-bromo-2-pentene, crotyl bromide, 3-bromo-2-methyl-1-propene, 3-bromo-1-trimethylsilylpropyne, and 4-bromo-3-methyl-1-butyne. Preferred are ethyl-2-methyl-2-bromo-propionate and (1-bromo-ethyl)benzene.

The compound represented by the general formula (2-2) is described below.

[Chem. 6]

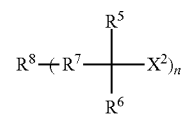

Formula (2-2)

In the formula (2-2), $R^5$ and $R^6$ each independently represent a hydrogen atom or an alkyl group having 1 to 8 carbon atoms, $X^2$ represents a halogen atom, $R^7$ represents an alkylene group having 1 to 8 carbon atoms, an arylene group, an amide group or an ester group, n is an integer of 2 to 4, and $R^8$ represents a divalent single bond or a divalent organic group when n is 2, represents a trivalent organic group when n is 3, and represents a tetravalent organic group when n is 4.

The group represented by $X^2$ in the general formula (2-2) is a halogen atom, such as fluorine, chlorine, bromine or iodine and is preferably a chlorine atom or a bromine atom.

The respective groups represented by $R^5$ and $R^6$ in the general formula (2-2) are each independently a hydrogen atom or an alkyl group having 1 to 8 carbon atoms, and examples of the alkyl group having 1 to 8 carbon atoms include: a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, and other linear or branched alkyl groups; and a cyclohexyl group and other cyclic alkyl groups. Linear or branched alkyl groups having 1 to 4 carbon atoms are preferred, and a methyl group or an ethyl group is more preferred.

The group represented by $R^7$ in the general formula (2-2) represents an alkylene group having 1 to 8 carbon atoms, an arylene group, an amide group or an ester group.

Examples of the alkylene group having 1 to 8 carbon atoms include: a methylene group, an ethylene group, an n-propylene group, an isopropylene group, an n-butylene group, an isobutylene group, a s-butylene group, a t-butylene group, an n-pentylene group, a 1-methyl-n-butylene group, a 2-methyl-n-butylene group, a 3-methyl-n-butylene group, a 1,1-dimethyl-n-propylene group, a 1,2-dimethyl-n-propylene group, a 2,2-dimethyl-n-propylene group, a 1-ethyl-n-propylene group, an n-hexylene group, a 1-methyl-n-pentylene group, a 2-methyl-n-pentylene group, a 3-methyl-n-pentylene group, a 4-methyl-n-pentylene group, a 1,1-dimethyl-n-butylene group, a 1,2-dimethyl-n-butylene group, a 1,3-dimethyl-n-butylene group, a 2,2-dimethyl-n-butylene group, a 2,3-dimethyl-n-butylene group, a 3,3-dimethyl-n-butylene group, a 1-ethyl-n-butylene group, a 2-ethyl-n-butylene group, a 1,1,2-trimethyl-n-propylene group, a 1,2,2-trimethyl-n-propylene group, a 1-ethyl-1-methyl-n-propylene group, a 1-ethyl-2-methyl-n-propylene group, and other linear or branched alkyl groups; and a cyclopropylene group, a cyclobutylene group, a cyclopentylene group, a cyclohexylene group, and other cyclic alkyl groups. Linear or branched alkylene groups having 1 to 4 carbon atoms are preferred, and a methylene group or an ethylene group is more preferred.

An example of the arylene group is a phenylene group.

An example of the amide group is —CONH—$R^{71}$—. $R^{71}$ is preferably an alkylene group having 1 to 8 carbon atoms and more preferably an alkylene group having 1 to 4 carbon atoms. Specific examples include a methylene group, an ethylene group, a trimethylene group, a tetramethylene group, a pentamethylene group, a hexamethylene group, and a heptamethylene group. The binding direction of the amide group is not particularly limited, but the binding mode of the amide group is preferably C—CO—NH—$R^{71}$—$R^8$.

An example of the ester group is —COO—$R^{72}$—. $R^{72}$ is preferably an alkylene group having 1 to 8 carbon atoms and more preferably an alkylene group having 1 to 4 carbon atoms. Specific examples include a methylene group, an ethylene group, a trimethylene group, a tetramethylene group, a pentamethylene group, a hexamethylene group, and a heptamethylene group. The binding direction of the ester group is not particularly limited, but the binding mode of the ester group is preferably C—COO—$R^{72}$—$R^8$.

There is no particular limitation as to $R^8$ in the general formula (2-2) so long as $R^8$ links a plurality of $R^7$ groups together. $R^8$ represents a divalent single bond or a divalent organic group when n is 2, represents a trivalent organic group when n is 3, and represents a tetravalent organic group when n is 4. Examples of the divalent organic group include groups represented by —NH—, —$CH_2$—, —O—, a phenylene group, and so on. Examples of the trivalent organic group include groups represented by —N<, —CH<, a phenylene group, and so on. Examples of the tetravalent organic group include groups represented by >C<, a phenylene group, and so on.

Specific examples of the compound represented by the general formula (2-2) include butanediol-bis(2-methyl-2-bromopropionate), 1,4-diphenyl-1,4-dibromobutane, 1,5-diphenyl-1,5-dibromoheptane, 1,6-diphenyl-1,6-dibromohexane, dibromoxylene, 1,4-diphenyl-1,4-dichlorobutane, 1,5-diphenyl-1,5-dichloroheptane, 1,6-diphenyl-1,6-dichlorohexane, and dichloroxylene.

Specifically, in the step (B), it is preferred that, under an inert gas atmosphere, an organic halogen compound is added into a reaction solution obtained by the step (A) and the solution is stirred to yield a reaction.

The reaction time differs depending on the reaction temperature and the pressure, but is preferably 5 minutes to 24 hours and more preferably 10 minutes to 2 hours. The reaction temperature is preferably −20° C. to 80° C., more preferably −10° C. to 20° C., and still more preferably −5° C. to 5° C. The pressure is normally an ordinary pressure, but may be an increased pressure or a reduced pressure.

Examples of the inert gas include nitrogen, argon, and helium and preferred inert gases are argon and nitrogen. When the step (B) is performed under an inert gas atmosphere, the yield of an organic tellurium compound can be further increased and the production of side products can be further reduced.

The usage rate of the organic halogen compound is normally 0.5 mol to 6 mol per mole of metallic tellurium. When the organic halogen compound is a compound represented by the general formula (2-1), the usage rate of the compound represented by the general formula (2-1) is, per mole of metallic tellurium, preferably 0.5 mol to 1.5 mol and more preferably 0.8 mol to 1.2 mol. When the organic halogen compound is a compound represented by the general formula (2-2), the usage rate of the compound represented by the general formula (2-2) is, per mole of metallic tellurium, preferably 1.5 mol to 6 mol and more preferably 1.8 mol to 4.8 mol.

After the step (B) is finished, an objective substance can be isolated by a known aftertreatment operation and a known separation and refinement means. For example, the objective substance can be obtained by subjecting the reaction liquid to separation by washing and then drying an obtained organic layer to concentrate it. Furthermore, if necessary, the obtained reaction product maybe refined by a known refining process, such as reduced-pressure distillation.

A specific example of the separation by washing is to mix a solvent capable of dissolving an organic tellurium compound with water and then withdraw the separated solvent. This operation enables the removal of water-soluble impurities from the organic tellurium compound and the repetition of the separation by washing makes the removal of impurities more effective. Examples of the solvent include: ester solvents, such as ethyl acetate; aromatic solvents, such as toluene and xylene; aliphatic hydrocarbons, such as hexane; and ethers, such as dialkyl ether.

In the step (A) of the production method according to the present invention, when, for example, metallic tellurium in powdered form is reacted with alkyl lithium, metallic tellurium is dissolved in a solvent by a reaction with a compound represented by the formula (1), so that a compound represented by a formula (3) (where $R^1$ and M in the formula (3) have the same meanings as $R^1$ and M, respectively, in the formula (1)) is obtained. Metallic tellurium is susceptible to surface oxidation and a large amount of oxide film on the surface of metallic tellurium makes the reaction inhomogeneous, resulting in undissolved powdered metallic tellurium residue. It can be assumed that, therefore, if the oxygen content in the metallic tellurium is kept low, the reaction can be more homogeneously promoted. In the step (B), a compound obtained by the step (A) and represented by the formula (3) is reacted with an organic halogen compound, thus obtaining an organic tellurium compound.

In the step (A) and/or the step (B), a compound represented by a formula (4) (where $R^1$ in the formula (4) has the same meaning as $R^1$ in the formula (1)) is obtained as a side product. The compound represented by the formula (4) is not only not involved in polymerization reaction, but also causes coloration of an organic tellurium compound and a polymer obtained by a living radical polymerization process using the organic tellurium compound. Particularly, when the organic tellurium compound is an oily matter, the compound represented by the formula (4) is difficult to remove by refinement. Therefore, the yield of the organic tellurium compound is further reduced by the refining process. It can be assumed that, in the production method according to the present invention, when the copper content of metallic tellurium is less than 100 ppm, although the reason is not clear, not only a catalytic action of such a slight amount of copper contained increases the yield of an organic tellurium compound, but also an unexpected effect of a reduction in the amount of production of the compound represented by the formula (4) (where $R^1$ in the formula (4) has the same meaning as $R^1$ in the formula (1)) can be obtained.

$$MR^1 + Te \rightarrow R^1TeM \qquad \text{Formula (3)}$$

$$R^1\text{—}Te\text{—}R^1 \qquad \text{Formula (4)}$$

(Organic Tellurium Compound)

By the method for producing an organic tellurium according to the present invention, an organic tellurium compound, for example, a compound represented by a general formula (5-1) or a compound represented by a general formula (5-2), can be produced in high yield and the production of side products (such as a compound represented by the formula (4)) can be reduced.

The compound represented by the general formula (5-1) can be used as a monofunctional living radical polymerization initiator. The compound represented by the general formula (5-2) can be used as a multifunctional living radical polymerization initiator. The term "monofunctional living radical polymerization initiator" used herein refers to a "compound including one group represented by —$TeR^1$ per molecule", while the term "multifunctional living radical polymerization initiator" used herein refers to a "compound including two or more groups each represented by —$TeR^1$ per molecule".

In the production method according to the present invention, when the content (mass ratio) of the compound of the general formula (4) in the organic tellurium compound is preferably not more than 5%, more preferably not more than 3%, and still more preferably not more than 1%, the use of the organic tellurium compound as a living radical polymerization initiator enables more certain reduction of coloration of the resultant polymer and thus more certain reduction of the adverse effect on the quality of the final product.

The compound represented by the general formula (5-1) is described below.

[Chem. 7]

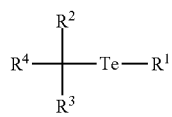

Formula (5-1)

In the formula (5-1), $R^1$ represents an alkyl group having 1 to 8 carbon atoms, an aryl group or an aromatic heterocyclic group, $R^2$ and $R^3$ each independently represent a hydrogen atom or an alkyl group having 1 to 8 carbon atoms, and $R^4$ represents an alkyl group having 1 to 8 carbon atoms, an aryl group, a substituted aryl group, an aromatic heterocyclic group, an alkoxy group, an acyl group, an amide group, an oxycarbonyl group, a cyano group, an allyl group or a propargyl group.

$R^1$ in the general formula (5-1) has the same meaning as $R^1$ in the general formula (1). $R^2$ to $R^4$ in the general formula (5-1) have the respective same meanings as $R^2$ to $R^4$ in the general formula (2-1).

Specific examples of the compound represented by the general formula (5-1) include (methyltelluromethyl) benzene, (methyltelluromethyl) naphthalene, ethyl-2-methyl-2-methyltellanyl-propionate, ethyl-2-methyl-2-n-butyltellanyl-propionate, (2-trimethylsiloxyethyl)-2-methyl-2-methyltellanyl-propionate, (2-hydroxyethyl)-2-methyl-2-methyltellanyl-propionate, and (3-trimethylsilylpropargyl)-2-methyl-2-methyltellanyl-propionate.

The compound represented by the general formula (5-2) is described below.

[Chem. 8]

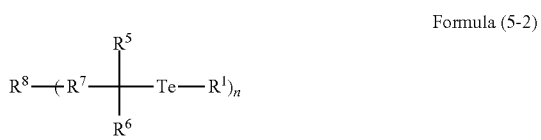

Formula (5-2)

In the formula (5-2), $R^1$ represents an alkyl group having 1 to 8 carbon atoms, an aryl group or an aromatic heterocyclic group, $R^5$ and $R^6$ each independently represent a hydrogen atom or an alkyl group having 1 to 8 carbon atoms, $R^7$ represents an alkylene group having 1 to 8 carbon atoms, an arylene group, an amide group or an ester group, n is an integer of 2 to 4, and $R^8$ represents a divalent single bond or a divalent organic group when n is 2, represents a trivalent organic group when n is 3, and represents a tetravalent organic group when n is 4.

$R^1$ in the general formula (5-2) has the same meaning as $R^1$ in the general formula (1). $R^5$ to $R^8$ and n in the general formula (5-2) have the respective same meanings as $R^5$ to $R^8$ and n in the general formula (2-2).

Specific examples of the compound represented by the general formula (5-2) include butanediol-bis(2-methyl-2-methyltellanyl-propionate), 1,4-diphenyl-1,4-dimethyltellurobutane, and dimethyltelluroxylene.

<Method for Producing Vinyl Polymer>

A method for producing a vinyl polymer according to the present invention is a production method including the step of polymerizing a vinyl monomer by living radical polymerization using an organic tellurium compound obtained by the method for producing an organic tellurium compound according to the present invention, for example, a compound represented by the general formula (5-1) and/or a compound represented by the general formula (5-2), to synthesize a vinyl polymer. In the living radical polymerization, polymerization may be performed by further adding an azo polymerization initiator and/or a compound represented by a general formula (6) (where $R^1$ in the formula (6) has the same meaning as $R^1$ in the formula (1)) depending on the type of the vinyl monomer for the purpose of reaction promotion, molecular weight control, and/or other purposes.

$$R^1\text{—}Te\text{—}Te\text{—}R^1 \qquad \text{Formula (6)}$$

A specific example is a method of producing a vinyl polymer by polymerizing a vinyl monomer using any one of (a) to (d) below:

(a) A compound represented by the general formula (5-1) and/or a compound represented by the general formula (5-2);

(b) A mixture of a compound represented by the general formula (5-1) and/or a compound represented by the general formula (5-2) and an azo polymerization initiator;

(c) A mixture of a compound represented by the general formula (5-1) and/or a compound represented by the general formula (5-2) and a compound represented by the general formula (6); and (d) A mixture of a compound represented by the general formula (5-1) and/or a compound represented by the general formula (5-2), an azo polymerization initiator, and a compound represented by the general formula (6).

The compound represented by the general formula (5-1) and/or the compound represented by the general formula (5-2) are as described above.

Specific examples of the compound represented by the general formula (6) include dimethyl ditelluride, diethyl ditelluride, di-n-propyl ditelluride, diisopropyl ditelluride, dicyclopropyl ditelluride, di-n-butyl ditelluride, di-s-butyl ditelluride, di-t-butyl ditelluride, dicyclobutyl ditelluride, diphenyl ditelluride, bis-(p-methoxyphenyl) ditelluride, bis-(p-aminophenyl) ditelluride, bis-(p-nitrophenyl) ditelluride, bis-(p-cyanophenyl) ditelluride, bis-(p-sulfonylphenyl) ditelluride, dinaphthyl ditelluride, and dipyridyl ditelluride.

Any azo polymerization initiator can be used without particular limitation so long as it is usable in usual radical polymerization. Examples include 2,2'-azobis-isobutyronitrile (AIBN), 2,2'-azobis(2-methylbutyronitrile) (AMBN), 2,2'-azobis(2,4-dimethylvaleronitrile) (ADVN), 1,1'-azobis(1-cyclohexanecarbonitrile) (ACHN), dimethyl-2,2'-azobis (isobutyrate) (MAIB), 4,4'-azobis(4-cyanovaleric acid) (ACVA), 1,1'-azobis(1-acetoxy-1-phenylethane), 2,2'-azobis(2-methylbutylamide), 2,2'-azobis(4-methoxy-2,4-dimethylvaleronitrile) (V-70), 2,2'-azobis(2-methylamidinopropane) dihydrochloride, 2,2'-azobis[2-(2-imidazoline-2-yl) propane], 2,2'-azobis[2-methyl-N-(2-hydroxyethyl) propionamide], 2,2'-azobis(2,4,4-trimethylpentane), 2-cyano-2-propylazoformamide, 2,2'-azobis(N-butyl-2-methylpropionamide), and 2,2'-azobis(N-cyclohexyl-2-methylpropionamide).

The vinyl monomer for use is not particularly limited so long as it is radically polymerizable and specific examples include vinyl monomers below.

Alternatively, the vinyl polymer obtained by the production method according to the present invention may be a copolymer composed of a plurality of vinyl monomers including vinyl monomers mentioned below.

The term "vinyl monomer" used herein refers to a monomer whose molecule has a radically polymerizable carbon-carbon double bond. The term "(meth)acryl" refers to "at least one of acryl and methacryl", "(meth)acrylic acid" refers to "at least one of acrylic acid and methacrylic acid", and "(meth)acrylate" refers to "at least one of acrylate and methacrylate".

Specific examples of the vinyl monomer are as follows:

(Meth)acrylates having a linear alkyl group, including methyl (meth)acrylate, ethyl (meth)acrylate, n-propyl (meth)acrylate, n-butyl (meth)acrylate, n-hexyl (meth)acrylate, n-octyl (meth)acrylate, n-nonyl (meth)acrylate, decyl (meth)acrylate, n-lauryl (meth)acrylate, and n-stearyl (meth)acrylate;

(Meth)acrylates having a branched alkyl group, including isopropyl (meth)acrylate, isobutyl (meth)acrylate, sec-butyl (meth)acrylate, tert-butyl (meth)acrylate, isooctyl (meth) acrylate, 2-ethylhexyl (meth)acrylate, isononyl (meth)acrylate, and isodecyl (meth)acrylate;

(Meth)acrylates having a cyclic alkyl group with a single-ring structure, including cyclohexyl (meth)acrylate, methylcyclohexyl (meth)acrylate, and cyclododecyl (meth)acrylate;

(Meth)acrylates having a cyclic alkyl group with a bridged-ring structure, including isobornyl (meth)acrylate, norbornyl (meth)acrylate, 1-adamantyl (meth)acrylate, and 2-adamantyl (meth)acrylate;

(Meth)acrylates having an aromatic ring group, including benzyl (meth)acrylate, phenyl (meth)acrylate, and phenoxyethyl (meth)acrylate;

(Meth)acrylates having a hydroxy group, including 2-hydroxyethyl (meth)acrylate, 3-hydroxypropyl (meth)acrylate, 2-hydroxypropyl (meth)acrylate, 4-hydroxybutyl (meth) acrylate, 6-hydroxyhexyl (meth)acrylate, 8-hydroxyoctyl (meth)acrylate, 10-hydroxydecyl (meth)acrylate, and 12-hydroxylauryl (meth)acrylate;

(Meth)acrylates having a polyalkylene glycol structural unit including: (meth)acrylates having a polyethylene glycol structural unit, such as polyethylene glycol (degree of polymerization: 2 to 10) methyl ether (meth)acrylate, polyethylene glycol (degree of polymerization: 2 to 10) ethyl ether (meth)acrylate, and polyethylene glycol (degree of polymerization: 2 to 10) propyl ether (meth)acrylate; and (meth)acrylates having a polypropylene glycol structural unit, such as polypropylene glycol (degree of polymerization: 2 to 10) methyl ether (meth)acrylate, polypropylene glycol (degree of polymerization: 2 to 10) ethyl ether (meth)acrylate, and polypropylene glycol (degree of polymerization: 2 to 10) propyl ether (meth)acrylate;

(Meth) acrylates having a lactone-modified hydroxy group, including 1 mol caprolactone adduct of 2-hydroxyethyl (meth)acrylate, 2 mol caprolactone adduct of 2-hydroxyethyl (meth)acrylate, 3 mol caprolactone adduct of 2-hydroxyethyl (meth)acrylate, 4 mol caprolactone adduct of 2-hydroxyethyl (meth)acrylate, 5 mol caprolactone adduct of 2-hydroxyethyl (meth)acrylate, and 10 mol caprolactone adduct of 2-hydroxyethyl (meth)acrylate;

(Meth)acrylates having an alkoxy group, including methoxyethyl (meth)acrylate and ethoxyethyl (meth)acrylate;

(Meth) acrylates having an oxygen-containing heterocyclic group, including glycidyl (meth)acrylate, tetrahydrofurfuryl (meth)acrylate, (3-ethyloxetane-3-yl)methyl (meth) acrylate, (2-methyl-2-ethyl-1,3-dioxolane-4-yl)methyl (meth)acrylate, cyclic trimethylolpropane formal (meth) acrylate, 2-[(2-tetrahydropyranyl)oxy]ethyl (meth)acrylate, and 1,3-dioxane (meth)acrylate;

(Meth)acrylic acid;

(Meth)acrylates having a carboxy group, including monomers formed by reacting hydroxyalkyl (meth)acrylate with an acid anhydride, such as maleic anhydride, succinic anhydride or phthalic anhydride;

(Meth)acrylates having a sulfonic acid group, including sulfonic acid ethyl (meth)acrylate;

(Meth)acrylates having a phosphoric acid group, including 2-(phosphonooxy)ethyl (meth)acrylate;

α-olefins, including 1-hexene, 1-octene, and 1-decene;

Aromatic vinyl monomers, including styrene, α-methylstyrene, 4-methylstyrene, 2-methylstyrene, 3-methylstyrene, 4-methoxystyrene, 2-hydroxymethylstyrene, and 1-vinylnaphthalene;

Hetero ring-containing vinyl monomers, including 2-vinylthiophene, N-methyl-2-vinylpyrrole, 1-vinyl-2-pyrrolidone, 2-vinylpyridine, and 4-vinylpyridine;

Vinylamides, including N-vinylformamide, N-vinylacetamide, and N-vinyl-ε-caprolactam;

Vinyl carboxylates, including vinyl acetate, vinyl pivalate, and vinyl benzoate;

Dienes, including butadiene, isoprene, 4-methyl-1,4-hexadiene, and 7-methyl-1,6-octadiene;

Tertiary amine-containing unsaturated monomers, including dimethylaminoethyl (meth)acrylate, dimethylaminopropyl (meth)acrylate, dimethylaminobutyl (meth) acrylate, diethylaminoethyl (meth)acrylate, diethylaminopropyl (meth)acrylate, diethylaminobutyl (meth)acrylate, and dimethylaminopropyl (meth)acrylamide;

Quaternary ammonium base-containing unsaturated monomers, including (meth)acryloyloxyethyltrimethyl ammonium chloride, (meth)acryloyloxypropyltrimethyl ammonium chloride, (meth)acryloyloxybutyltrimethyl ammonium chloride, (meth)acryloyloxyethylbenzyldimethyl ammonium chloride, (meth)acryloyloxypropylbenzyldimethyl ammonium chloride, (meth)acryloyloxybutylbenzyldimethyl ammonium chloride, (meth)acryloyloxyethylbenzyldiethyl ammonium chloride, (meth)acryloyloxypropylbenzyldiethyl ammonium chloride, (meth)acryloyloxybutylbenzyldiethyl ammonium chloride, (meth)acryloylamidopropylbenzyldimethyl ammonium chloride, (meth)acryloyloxyethyltrimethyl ammonium bromide, (meth)acryloyloxypropyltrimethyl ammonium bromide, (meth)acryloyloxybutyltrimethyl ammonium bromide, (meth)acryloyloxyethylbenzyldimethyl ammonium bromide, (meth)acryloyloxypropylbenzyldimethyl ammonium bromide, (meth)acryloyloxybutylbenzyldimethyl ammonium bromide, (meth)acryloyloxyethylbenzyldiethyl ammonium bromide, (meth)acryloyloxypropylbenzyldiethyl ammonium bromide, (meth)acryloyloxybutylbenzyldiethyl ammonium bromide, (meth)acryloylamidopropylbenzyldimethyl ammonium bromide, (meth)acryloyloxyethyltrimethyl ammonium iodide, (meth)acryloyloxypropyltrimethyl ammonium iodide, (meth)acryloyloxybutyltrimethyl ammonium iodide, (meth)acryloyloxyethylbenzyldimethyl ammonium iodide, (meth)acryloyloxypropylbenzyldimethyl ammonium iodide, (meth)acryloyloxybutylbenzyldimethyl ammonium iodide, (meth)acryloyloxyethylbenzyldiethyl ammonium iodide, (meth)acryloyloxypropylbenzyldiethyl ammonium iodide, (meth)acryloyloxybutylbenzyldiethyl ammonium iodide, (meth)acryloyloxyethyltrimethyl ammonium fluoride, (meth)acryloyloxypropyltrimethyl ammonium fluoride, (meth)acryloyloxybutyltrimethyl ammonium fluoride, (meth)acryloyloxyethylbenzyldimethyl ammonium fluoride, (meth)acryloyloxypropylbenzyldimethyl ammonium fluoride, (meth)acryloyloxybutylbenzyldimethyl ammonium fluoride, (meth)acryloyloxyethylbenzyldiethyl ammonium fluoride, (meth)acryloyloxypropylbenzyldiethyl ammonium fluoride, (meth)acryloyloxybutylbenzyldiethyl ammonium fluoride, (meth)acryloyloxyethyltrimethyl ammonium methylsulfate, (meth)acryloyloxypropyltrimethyl ammonium methylsulfate, (meth)acryloyloxybutyltrimethyl ammonium methylsulfate, (meth)acryloyloxyethyldimethylethyl ammonium ethylsulfate, (meth)acryloyloxypropyldimethylethyl ammonium ethylsulfate, (meth)acryloyloxybutyldimethylethyl ammonium ethylsulfate, (meth)acryloyloxyethyltrimethyl ammonium toluene-4-sulfonate, (meth)acryloyloxypropyltrimethyl ammonium toluene-4-sulfonate, (meth)acryloyloxybutyltrimethyl ammonium toluene-4-sulfonate, (meth)acryloylamidopropyltrimethyl ammonium methylsulfate, and (meth)acryloylamidopropylethyldimethyl ammonium ethylsulfate.

(Meth)acrylamides, including (meth)acrylamide, N-methyl(meth)acrylamide, N-isopropyl(meth)acrylamide, and N,N-dimethyl(meth)acrylamide;

Halogenated vinyl monomers, including vinyl fluoride, vinylidene fluoride, trifluoroethylene, chlorotrifluoroethylene, tetrafluoroethylene, hexafluoropropylene, tetrafluoropropylene, vinylidene chloride, vinyl chloride, 1-chloro-1-fluoroethylene, and 1,2-dichloro-1,2-difluoroethylene.

Preferred among the above vinyl monomers are (meth)acrylates having a linear alkyl group, (meth)acrylates having a branched alkyl group, (meth)acrylates having a cyclic alkyl group with a single-ring structure, (meth)acrylates having an aromatic ring group, (meth)acrylates having a hydroxy group, (meth)acrylates having a polyalkylene glycol structural unit, (meth)acrylates having a lactone-modified hydroxy group, (meth)acrylates having an alkoxy group, (meth)acrylates having an oxygen-containing heterocyclic group, (meth)acrylic acid, aromatic vinyl monomers, hetero ring-containing vinyl monomers, vinylamides, tertiary amine-containing unsaturated monomers, and (meth)acrylamides.

In the polymerization process, a vinyl monomer and a compound represented by the general formula (5-1) and/or a compound represented by the general formula (5-2) are mixed in a vessel inside of which the atmosphere is replaced with an inert gas, and, depending on the type of the vinyl monomer and for the purpose of promoting the reaction, controlling the molecular weight or other purposes, an azo polymerization initiator and/or a compound represented by the general formula (6) are further mixed in the vessel. In doing so, examples of the inert gas include nitrogen, argon, and helium. Argon or nitrogen is preferred. Nitrogen is particularly preferred.

The amount of the vinyl monomer used in the above cases of (a), (b), (c), and (d) may be appropriately adjusted according to the physical properties of a desired copolymer. The amount of the vinyl monomer is, per mole of the compound represented by the general formula (5-1) and/or the compound represented by the general formula (5-2), preferably 5 mol to 10,000 mol.

In using a compound represented by the general formula (5-1) and/or a compound represented by the general formula (5-2) in conjunction with an azo polymerization initiator in the above case (b), the amount of azo polymerization initiator used is, per mole of the compound represented by the general formula (5-1) and/or the compound represented by the general formula (5-2), preferably 0.01 mol to 10 mol.

In using a compound represented by the general formula (5-1) and/or a compound represented by the general formula (5-2) in conjunction with a compound represented by the general formula (6) in the above case (c), the amount of compound represented by the general formula (6) is, per mole of the compound represented by the general formula (5-1) and/or the compound represented by the general formula (5-2), preferably 0.01 mol to 100 mol.

In using a compound represented by the general formula (5-1) and/or a compound represented by the general formula (5-2) in conjunction with a compound represented by the general formula (6) and an azo polymerization initiator in the above case (d), the amount of compound represented by the general formula (6) is, per mole of the compound represented by the general formula (5-1) and/or the compound represented by the general formula (5-2), preferably 0.01 mol to 100 mol and the amount of azo polymerization initiator used is, per mole of the compound represented by the general formula (5-1) and/or the compound represented by the general formula (5-2), preferably 0.01 mol to 10 mol.

The polymerization reaction can be performed even in the absence of solvent, but may be performed, using an aprotic solvent or protic solvent commonly used for radical polymerization, by stirring the above mixture. Examples of the aprotic solvent that can be used include anisole, benzene, toluene, N,N-dimethylformamide (DMF), dimethylsulfoxide (DMSO), acetone, 2-butanone (methyl ethyl ketone), dioxane, propylene glycol monomethyl ether acetate, chloroform, carbon tetrachloride, tetrahydrofuran (THF), ethyl acetate, and trifluoromethylbenzene. Examples of the protic solvent include water, methanol, ethanol, isopropanol, n-butanol, ethyl cellosolve, butyl cellosolve, 1-methoxy-2-propanol, hexafluoroisopropanol, and diacetone alcohol.

The amount of solvent used may be appropriately adjusted and is, for example, per gram of vinyl monomer, preferably not less than 0.01 ml, more preferably not less than 0.05 ml, still more preferably not less than 0.1 ml, preferably not more than 50 ml, more preferably not more than 10 ml, and still more preferably not more than 1 ml.

The reaction temperature and the reaction time may be appropriately adjusted depending on the molecular weight or molecular weight distribution of a desired copolymer, but the mixture is preferably stirred at 0° C. to 150° C. for 1 minute to 100 hours. The TERP process can provide a high yield and an accurate molecular weight distribution even at a low polymerization temperature and even for a short polymerization time. In doing so, the pressure is normally an ordinary pressure, but may be an increased pressure or a reduced pressure.

Because the growing ends of the vinyl polymer to be obtained by the above polymerization have the form of —TeR$^1$ (where R$^1$ is the same as described previously and —TeR$^1$ is hereinafter referred to as a tellurium group) derived from a compound represented by the general formula (5-1) and/or a compound represented by the general formula (5-2), the groups can be used as a macro living radical polymerization initiator. In other words, an A-B diblock copolymer, an A-B-A triblock copolymer, an A-B-C triblock copolymer, and so on can be produced using a macro living radical polymerization initiator.

Operations in the air after the end of the polymerization reaction gradually deactivate the growing ends of the vinyl polymer obtained by the polymerization reaction, but tellurium atoms may still remain at the growing ends. Because the vinyl polymer with tellurium atoms remaining at the ends is colored and has poor thermal stability, the tellurium atoms should preferably be removed.

As the method for removing the tellurium atoms, a radical reduction method using tributylstannane, a thiol compound or the like, a method for adsorbing tellurium atoms with activated carbon, silica gel, activated alumina, activated white earth, molecular sieves, a polymer adsorbent or the like, a method for adsorbing metal with an ion-exchange resin or the like, a liquid-liquid extraction method or solid-liquid extraction method for oxidatively separating tellurium atoms at the ends of the vinyl polymer by addition of a peroxide, such as hydrogen peroxide water or benzoyl peroxide, or injection of air or oxygen into the system and then removing the residual tellurium compound by water rinse or a combination of appropriate solvents, or a solution-phase purification method, such as ultrafiltration for extracting and removing only molecules having a molecular weight equal to or less than a specified molecular weight, can be used or these methods can be variously combined.

When a compound represented by the general formula (5-1) is used as a living radical polymerization initiator, the other ends (the opposite ends of the growing ends) of the vinyl polymer obtained by the polymerization reaction has the form of —CR$^2$R$^3$R$^4$ (where R$^2$, R$^3$, and R$^4$ are the same as R$^2$, R$^3$, and R$^4$, respectively, in the formula (5-1)) derived from an organic tellurium compound.

When, in the method for producing a vinyl polymer according to the present invention, a compound represented by the general formula (5-1) and/or a compound represented by the general formula (5-2) is used as a living polymerization initiator, the content of a compound represented by the general formula (4) in the living polymerization initiator is small, so that the coloration of the resultant vinyl polymer can be reduced. The content of the compound represented by the general formula (4) in the living polymerization initiator is preferably not more than 10% and more preferably not more than 6%. There is no particular limitation as to the lower limit of the content of the compound represented by the general formula (4) in the living polymerization initiator, but a lower value is more preferred. Therefore, the lower limit of the content of the compound represented by the general formula (4) in the living polymerization initiator may be, for example, 0%.

Since the vinyl polymer obtained by the method for producing a vinyl polymer according to the present invention can be reduced in coloration derived from an organic tellurium compound, it can be suitably used for a dispersant for a color filter, a dispersant for an ink-jet printer, a pressure-sensitive adhesive for optical components, and so on.

EXAMPLES

Hereinafter, a detailed description will be given of the present invention with reference to examples, but the present invention is not limited to these examples.

The oxygen content of metallic tellurium was obtained by measuring the tellurium content with an X-ray fluorescence spectrometer (trade name: ZSX Primus II, manufactured by Rigaku Corporation) and making a calculation regarding the remaining component as oxygen.

The copper content of metallic tellurium was measured, after the heating of the metallic tellurium to melt with nitric acid, with an ICP mass spectrometer (trade name: PlasmaQuant MS Elite, manufactured by Analytik Jena). Specifically, 0.5 g of metallic tellurium was weighed accurately to 0.1 mg into an asking Teflon (registered trademark) vessel and moist-heated to melt at 240° C. for 10 minutes in 5 mL of 69% high-purity nitric acid with a microwave sample preparation system (trade name: START D, by Milestone General), thus completely dissolving metallic tellurium in nitric acid. The solution was fixed to a volume of 50 mL with ultrapure water and 1 mL of sample was taken from the solution, diluted 20-fold with ultrapure water, and measured in terms of copper content with an ICP mass spectrometer.

The specific surface area of metallic tellurium was measured by the BET method with a surface area analyzer (trade name: TriStar II 3020, manufactured by Shimadzu Corporation).

<Production of Organic Tellurium Compound>

Example 1

Under a nitrogen atmosphere, 6.38 g (50 mmol) of metallic tellurium (oxygen content: 2%, copper content: 1 ppm) was suspended in 50 mL of tetrahydrofuran. An amount of 34.4 mL (55 mmol) of n-butyl lithium (1.6 M solution thereof in hexane) was added slowly (over 10 minutes) dropwise into the obtained suspension on ice (at 0° C.). The obtained reaction solution was stirred on ice (at 0° C.) until metallic tellurium completely disappeared (for 20 minutes). An amount of 10.7 g (55 mmol) of ethyl-2-methyl-2-bromo-propionate was added into the reaction solution on ice (at 0° C.) and the mixture was stirred on ice (at 0° C.) for 2 hours. After the end of the reaction, the reaction solution was returned to room temperature (23° C.), 20 mL of water and 15 mL of ethyl acetate were added to the reaction solution, the mixture liquid was stirred for 5 minutes, then allowed to stand still, and thus separated into two layers, and a water layer as a heavy liquid was withdrawn. Similar liquid separation by water washing was repeated twice and an ethyl acetate layer as a light liquid was concentrated in vacuum, thus obtaining 13.28 g of oily matter.

When analyzed with $^1$H-NMR (trade name: AVANCE 500, manufactured by Bruker Corporation), the oily matter was ethyl-2-methyl-2-n-butyltellanyl-propionate (hereinafter referred to as "BTEE") (yield: 88%) and dibutyl telluride (Bu$_2$Te) (yield: 4.0%). The results are shown in Table 1.

Examples 2 to 8

The same operation as in Example 1 was performed except that metallic tellurium having exhibited an oxygen content and a copper content shown in Table 1 in the measurements with the X-ray fluorescence spectrometer and the ICP mass spectrometer was selected and used in place of metallic tellurium in Example 1, so that an oily matter was obtained. The results are shown in Table 1. The measurements with the X-ray fluorescence spectrometer and the ICP mass spectrometer were conducted in the same manners as in Example 1.

Comparative Examples 1 to 2

The same operation as in Example 1 was performed except that metallic tellurium having exhibited an oxygen content and a copper content shown in Table 1 in the measurements with the X-ray fluorescence spectrometer and the ICP mass spectrometer was selected and used in place of metallic tellurium in Example 1, so that an oily matter was obtained. A slight amount of metallic tellurium remained in the reaction solution after dropwise addition of n-butyl lithium. The results are shown in Table 1. The measurements with the X-ray fluorescence spectrometer and the ICP mass spectrometer were conducted in the same manners as in Example 1.

TABLE 1

| | Source Material (Metallic Tellurium) | | | Yields of Reaction Products | |
|---|---|---|---|---|---|
| | oxygen content (%) | copper content (ppm) | SSA (m$^2$/g) | BTEE (%) | Bu$_2$Te (%) |
| Ex. 1 | 2 | 1 | 1.2 | 88 | 4.0 |
| Ex. 2 | 2 | 3 | 1.2 | 92 | 2.2 |
| Ex. 3 | 2 | 14 | 1.2 | 94 | 0.8 |
| Ex. 4 | 2 | 17 | 1.2 | 94 | 0.8 |
| Ex. 5 | 2 | 21 | 1.2 | 94 | 2.3 |
| Ex. 6 | 2 | 36 | 1.2 | 92 | 2.9 |
| Ex. 7 | 2 | 55 | 1.2 | 86 | 4.6 |
| Ex. 8 | 2 | 83 | 1.2 | 87 | 5.1 |
| Comp. Ex. 1 | 3 | 100 | 1.2 | 71 | 13.2 |
| Comp. Ex. 2 | 2 | 102 | 1.2 | 76 | 11.1 |

<Production of Vinyl Polymer>

Using each of the organic tellurium compounds (oily matters) obtained in Examples 1 to 8, methyl acrylate was polymerized by living radical polymerization, thus obtaining vinyl polymers. It was visually confirmed that all the obtained vinyl polymers were not colored.

Using each of the organic tellurium compounds obtained in Comparative Examples 1 to 2, methyl acrylate was polymerized by living radical polymerization, thus obtaining vinyl polymers. It was visually confirmed that all the obtained vinyl polymers were colored.

The invention claimed is:

1. A method for producing an organic tellurium compound, the method comprising the steps of: (A) reacting metallic tellurium with a compound represented by formula (1) below; and (B) reacting a compound obtained by the step (A) with an organic halogen compound, the metallic tellurium having a copper content of not less than 0.1 ppm and less than 100 ppm and an oxygen content of not less than 0.1 wt. % and less than 3 wt. %, $$M(R^1)m \qquad \text{Formula (1)}$$

where $R^1$ represents an alkyl group having 1 to 8 carbon atoms, an aryl group or an aromatic heterocyclic group, M represents an alkali metal or an alkaline earth metal, m represents 1 when M is an alkali metal, and m represents 2 when M is an alkaline earth metal.

2. The method for producing an organic tellurium compound according to claim 1, wherein the organic halogen compound is at least one selected from the group consisting of a compound represented by formula (2-1) below and a compound represented by formula (2-2) below,

[Chem. 1]

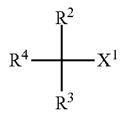

Formula (2-1)

where $R^2$ and $R^3$ each independently represent a hydrogen atom or an alkyl group having 1 to 8 carbon atoms, $R^4$ represents an alkyl group having 1 to 8 carbon atoms, an aryl group, a substituted aryl group, an aromatic heterocyclic group, an alkoxy group, an acyl group, an amide group, an oxycarbonyl group, a cyano group, an allyl group or a propargyl group, and $X^1$ represents a halogen atom,

[Chem. 2]

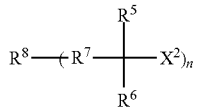

Formula (2-2)

where $R^5$ and $R^6$ each independently represent a hydrogen atom or an alkyl group having 1 to 8 carbon atoms, $X^2$ represents a halogen atom, $R^7$ represents an alkylene group having 1 to 8 carbon atoms, an arylene group, an amide group or an ester group, n is an integer of 2 to 4, and $R^8$ represents a divalent single bond or a divalent organic group when n is 2, represents a trivalent organic group when n is 3, and represents a tetravalent organic group when n is 4.

3. The method for producing an organic tellurium compound according to claim 1, wherein a usage rate of the compound represented by the general formula (1) is 0.5 mol to 1.5 mol per mole of the metallic tellurium.

4. The method for producing an organic tellurium compound according to claim 1, wherein a usage rate of the organic halogen compound is 0.5 mol to 6 mol per mole of the metallic tellurium.

5. The method for producing an organic tellurium compound according to claim 1, wherein a specific surface area of the metallic tellurium is 0.5 m$^2$/g to 2.0 m$^2$/g.

6. The method for producing an organic tellurium compound according to claim 1, wherein the step (A) is performed by suspending the metallic tellurium in a solvent.

7. A living radical polymerization initiator being an organic tellurium compound obtained by the method according to claim 1.

8. A method for producing a vinyl polymer, the method comprising the step of polymerizing a vinyl monomer by living radical polymerization using the organic tellurium compound obtained by the method according to claim 1 to synthesize a vinyl polymer.

9. A vinyl polymer produced by the method for producing a vinyl polymer according to claim 8.

10. The method for producing an organic tellurium compound according to claim 1, wherein the steps (A) and (B) are performed under an inert gas atmosphere.

* * * * *